United States Patent
Wilsey et al.

(10) Patent No.: US 8,771,793 B2
(45) Date of Patent: Jul. 8, 2014

(54) VACUUM ASSISTED SLOT DIE COATING TECHNIQUES

(75) Inventors: Christopher D. Wilsey, Carmel, IN (US); Abner D. Joseph, Carmel, IN (US); Sergio Buccilli, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 215 days.

(21) Appl. No.: 13/088,078

(22) Filed: Apr. 15, 2011

(65) Prior Publication Data

US 2012/0263879 A1  Oct. 18, 2012

(51) Int. Cl.
*B05D 3/00* (2006.01)

(52) U.S. Cl.
USPC .................................. 427/294; 427/296

(58) Field of Classification Search
USPC .......................... 427/294, 296, 402
See application file for complete search history.

(56) References Cited

U.S. PATENT DOCUMENTS

| | | | |
|---|---|---|---|
| 5,154,951 A | 10/1992 | Finnicum et al. | |
| 5,558,716 A | 9/1996 | Mitani et al. | |
| 6,524,388 B1 | 2/2003 | Yamada et al. | |
| 6,576,296 B1 * | 6/2003 | Yapel et al. | 427/294 |
| 6,676,995 B2 | 1/2004 | Dick et al. | |
| 6,689,411 B2 | 2/2004 | Dick et al. | |
| 6,824,828 B2 | 11/2004 | Su et al. | |
| 7,073,246 B2 | 7/2006 | Bhullar et al. | |
| 7,727,467 B2 | 6/2010 | Burke et al. | |
| 7,749,437 B2 | 7/2010 | Mosoiu et al. | |
| 7,879,619 B2 | 2/2011 | Jing et al. | |
| 2002/0150792 A1 | 10/2002 | Kolb et al. | |
| 2005/0008537 A1 * | 1/2005 | Mosoiu et al. | 422/56 |
| 2007/0234954 A1 | 10/2007 | Ciliske et al. | |
| 2012/0000420 A1 | 1/2012 | Ikagawa et al. | |

FOREIGN PATENT DOCUMENTS

| | | |
|---|---|---|
| EP | 1 062 544 B1 | 6/2004 |
| EP | 1 316 367 B1 | 8/2007 |
| JP | 2004-358380 | 12/2004 |
| WO | WO 95/29763 | 11/1995 |
| WO | WO 95/29764 | 11/1995 |
| WO | WO 2009/143132 A2 | 11/2009 |
| WO | WO 2010/100285 A1 | 9/2010 |
| WO | WO 2010/106979 A1 | 9/2010 |

* cited by examiner

*Primary Examiner* — Dah-Wei D Yuan
*Assistant Examiner* — Nga Leung V Law
(74) *Attorney, Agent, or Firm* — Krieg DeVault LLP

(57) ABSTRACT

Systems, apparatuses, techniques and processes for applying a wet film to a substrate using a slot die are provided. In one form, the air pressure around at least a portion of the discharge end of the slot die is adjustable by the application of a vacuum force in order to control the width and thickness of the wet film being applied to the substrate. In one aspect of this form, the wet film is a narrow, continuous stripe of reagent material applied to a moving web of the substrate from which a plurality of test elements will be obtained. However, different forms and applications are also envisioned.

18 Claims, 10 Drawing Sheets

VACUUM ASSISTED SLOT DIE COATING TECHNIQUES

BACKGROUND

The use of disposable test elements has become commonplace to measure the presence and/or concentrations of selected analytes in test samples. For example, patients suffering from diabetes and similar medical conditions often engage in self-monitoring of blood glucose wherein the patient monitors his or her blood glucose levels. The purpose of monitoring the blood glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals. Failure to test blood glucose levels properly and on a regular basis can result in serious diabetes-related complications, including cardiovascular disease, kidney disease, nerve damage and blindness.

A number of analyte measurement systems are currently available that, in combination with a disposable test element, permit an individual to test or measure for a targeted analyte in a test sample. For example, a disposable test element can be used with a glucose meter to measure the amount of glucose in a blood sample electrochemically or optically. In current glucose meters, the information displayed as a consequence of a successful blood glucose measurement is the respective blood glucose value, typically shown in mg/dL or mmol units, and perhaps the time and date the measurement was performed. This information in combination with calculation of planned or known intake of carbohydrates or planned or known activities and knowledge of other situational or individual factors is in most cases sufficient to allow diabetics to adjust or derive their dietary intake and/or an immediate dose of insulin to inject to control blood glucose level on the short-term. Also, in case of low glucose values, diabetics can detect the need for intake of sugar to avoid hypoglycemia.

Current trends in analyte testing and test elements require smaller test samples and faster analysis times. In the case of diabetics for example, this provides a significant benefit to the patient, allowing the use of smaller blood samples that can be obtained from less sensitive areas of the body. Additionally, faster test times and more accurate results enable patients to better control their blood sugar level.

In one form, disposable test elements used with meters for electrochemically measuring the amount of glucose in the blood sample include an electrode arrangement and a coating of a reagent material for producing an electrochemical signal in the presence of glucose. Numerous variations of the reagent coating are possible depending upon the specific analyte(s) to be tested, and there are typically numerous chemistries available for use with each of the various analytes. Generally speaking, however, it is desirable to form the reagent layer in the test strip or biosensor as thin and as uniform as possible. For example, a thinner reagent layer will hydrate more quickly and will therefore produce a quicker test result. In addition, variations in thickness of the reagent layer increasingly affect the accuracy of the test result. As a result, non-uniformities in the reagent layer can lead to inconsistency in filling a sample receiving chamber of the test element, prolonged dissolution intervals, and inconsistent mixing of the reagent with the sample fluid, and, ultimately, poor test results.

Nonetheless, while forming a thin and uniform reagent layer that hydrates quickly with a small volume is desirable, it is not easily obtained because of the difficulties in working with small volumes of liquid reagent, variations in the substrate material of the test elements, and limitations in processing equipment. For example, when the reagent layer is applied to a test element by a slot die coating process, current attempts at achieving thickness uniformity of the reagent layer on the substrate of the test element are made by moving the slot die relative to the substrate in order to adjust the thickness of the reagent layer in response to, for example, thickness variations of the substrate. However, the ability to control thickness uniformity of the reagent layer by this approach is limited because movement of the slot die relative to the substrate can often be delayed and/or result in a reduced coating gap between the discharge end of the slot die and the substrate, which can result in wet film deformities, such as streaking, caused by debris trapped between the slot die and the substrate and/or otherwise impact the coating process due to variations in the thickness of the substrate.

With regard to a slot die coating process, certain other methods and parameters relating to the reagent coating layer itself are also known to facilitate thickness uniformity. See, e.g., U.S. Pat. No. 7,749,437 and U.S. Pat. No. 7,879,619, the disclosures of which are hereby incorporated herein by reference in their entireties.

In view of the foregoing, and given the ramifications of accurately analyzing selected analytes in test samples, there remains a need for improvements in the application of the reagent layer on test elements.

SUMMARY

Systems, apparatuses, techniques and processes for applying a wet film to a substrate using a slot die are provided. In one aspect, the air pressure around at least a portion of the discharge end of the slot die is adjustable in order to control the width and thickness of the wet film being applied to the substrate. Among other things, this technique allows the coating gap between the discharge end of the slot die and the substrate to be increased, which results in reduced wet film deformities, such as streaking, caused by debris trapped between the slot die and the substrate. Increased coating gaps also reduce the impact that variations in the substrate thickness have on the coating process. In addition, the ability to control the width and thickness of the wet film also increases thickness uniformity along the substrate which, in the case of the substrate being used to form test elements for measuring the presence and/or concentrations of selected analytes in test samples, results in greater lot to lot consistency and accuracy in the test elements.

In one aspect, a method for applying a wet film to a substrate includes applying a coating material from a discharge end of a slot die onto a moving web of the substrate to form the wet film on the substrate. The wet film includes a width and a thickness relative to the substrate. The method also includes applying a vacuum force adjacent the discharge end of the slot die and adjusting the vacuum force in real-time while applying the coating material to control the width and thickness of the wet film.

In one refinement of the aspect the method further includes sensing the width of the wet film, and adjusting the vacuum force is performed in response to determining the width corresponds to a value other than a predetermined value.

In another refinement of the aspect the predetermined value is about 5 millimeters.

In another refinement of the aspect the predetermined value is about 7 millimeters.

In another refinement of the aspect the predetermined value is between about 4.7 millimeters and about 5.3 millimeters.

In another refinement of the aspect the predetermined value is between about 6.7 millimeters and about 7.5 millimeters.

In another refinement of the aspect the substrate is formed of a polymer material on which a plurality of electrode patterns is positioned.

In another refinement of the aspect the method further includes applying the coating material from the discharge end of the slot die over the electrode patterns to form the wet film on the electrode patterns.

In another refinement of the aspect applying the vacuum force includes positioning a vacuum box adjacent the discharge end of the slot die. The vacuum box includes a pair of vacuum outlets positioned opposite one another and upstream from the wet film.

In another refinement of the aspect the method further includes maintaining a constant coating gap between the slot die and the moving web.

In another refinement of the aspect the coating gap is between about 40 μm and about 450 μm.

In another refinement of the aspect the coating material includes a reagent for producing an electrochemical signal in the presence of a test analyte.

In another refinement of the aspect the test analyte is glucose and the reagent includes at least one of an enzyme, co-enzyme and co-factor.

In another refinement, the thickness of the wet film is between about 40 μm and about 100 μm.

In another refinement, the method further includes drying the wet film to provide a dried layer of the coating material on the substrate. The dried layer of the coating material includes a dried thickness between about 3 μm and about 20 μm.

In another refinement, applying the vacuum force creates a pressure differential between an upstream side of the discharge end and a downstream side of the discharge end.

In a further aspect, an apparatus for applying a wet film to a substrate includes a slot die positionable adjacent to the substrate and including a discharge end from which a coating material is dischargeable onto the substrate to form the wet film. The apparatus also includes an air pressure regulation system operable to control width and thickness of the wet film relative to the substrate by adjusting air pressure adjacent the discharge end of the slot die as the coating material is discharged onto the substrate.

In one refinement of the aspect the air pressure regulation system includes an enclosure at least partially surrounding the discharge end of said slot die, and a vacuum source coupled with the enclosure.

In another refinement of the aspect the apparatus further includes a sensor configured to determine the width of the wet stripe and provide a corresponding sensor signal representative of the width. The apparatus also includes a controller responsive to the sensor signal to adjust an amount of vacuum applied by the vacuum source to the enclosure when the sensor signal is representative of a width that corresponds to a value other than a predetermined value.

In another refinement of the aspect the predetermined value is between about 4.7 millimeters and about 5.3 millimeters.

In another refinement of the aspect the predetermined value is between about 6.7 millimeters and about 7.5 millimeters.

In another refinement of the aspect the vacuum source is coupled with the enclosure at a location upstream from the wet film.

In another refinement of the aspect the enclosure includes a pair of vacuum outlets positioned opposite one another.

In another refinement of the aspect the apparatus further includes a moving web of the substrate with the web being formed of a polymer material on which a plurality of electrode patterns is positioned. The slot die is positionable over the electrode patterns such that the coating material is dischargeable from the discharge end to form the wet film on the electrode patterns.

In another refinement of the aspect a coating gap in the range of about 40 μm to about 450 μm extends between the discharge end of the slot die and the substrate.

In another refinement of the aspect the apparatus further includes a roller system operable to move a web of the substrate relative to the slot die.

In another refinement of the aspect the apparatus further includes a reservoir containing a quantity of the coating material, and the coating material includes a reagent for producing an electrochemical signal in the presence of a test analyte.

In another refinement of the aspect the test analyte is glucose and the reagent includes at least one of an enzyme, co-enzyme and co-factor.

In another aspect, a method for applying a wet film to a substrate includes applying a coating material from a discharge end of a slot die onto the substrate to form the wet film on the substrate; controlling a thickness of the wet film relative to the substrate by adjusting a pressure differential existing between an upstream side of the slot die and a downstream side of the slot die; and maintaining a constant coating gap between the discharge end of the slot die and the substrate while controlling the thickness of the wet film.

In one refinement of the aspect adjusting the pressure differential includes changing an amount of vacuum applied adjacent to the upstream side of the discharge end of the slot die.

In another refinement of the aspect adjusting the pressure differential is performed in response to determining that a width of the wet film corresponds to a value other than a predetermined value.

In another refinement of the aspect the predetermined value is between about 2.5 millimeters and 7.5 millimeters.

In another refinement of the aspect the method further includes maintaining a constant flow rate of the coating material through the slot die while controlling the thickness of the wet film.

In another refinement of the aspect the method further includes moving the substrate relative to the slot die, and maintaining a constant rate of movement of the substrate relative to the slot die while controlling the thickness of the wet film.

In another refinement of the aspect the coating gap is between about 40 μm and about 450 μm.

In another refinement of the aspect the coating material includes a reagent for producing an electrochemical signal in the presence of a test analyte.

Another aspect of the present application is a unique technique for forming test elements useful for measuring the presence and/or concentrations of selected analytes in test samples. Other aspects include unique methods, systems, devices, kits, assemblies, equipment, and/or apparatus related to slot die coating processes, including those used to apply a reagent material to a test element.

Further aspects, embodiments, forms, features, benefits, objects, and advantages shall become apparent from the detailed description and figures provided herewith.

DETAILED DESCRIPTION OF THE ILLUSTRATED EMBODIMENTS

Figure 1:
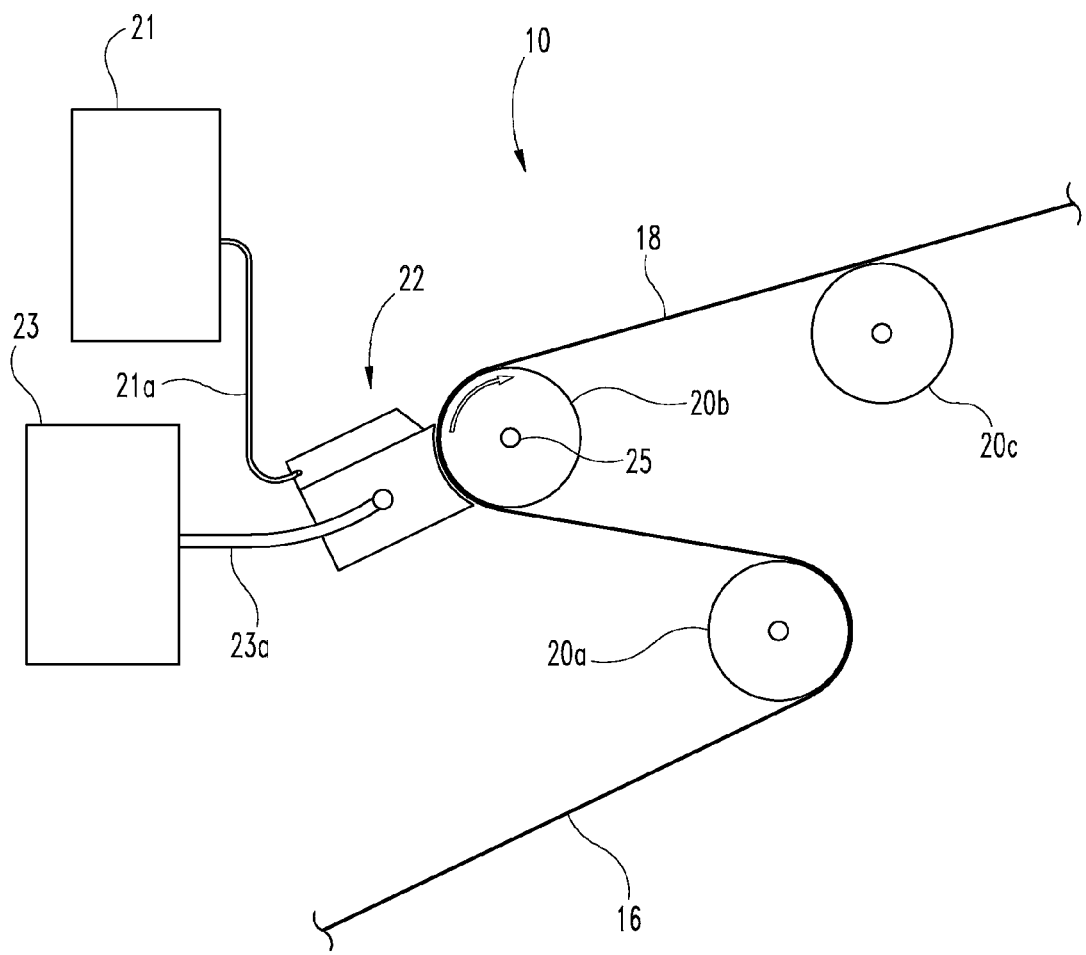
FIG. 1 is a diagrammatic illustration of a slot die coating apparatus.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Systems, apparatuses, techniques and processes for applying a wet film of a coating material to a substrate using a slot die are provided. In one aspect, air pressure adjacent to and/or around a discharge end of the slot die are regulated in order to control the width and thickness of the wet film of coating material that is being applied to the substrate. More particularly, in one form, a vacuum source is applied to an upstream side of the slot die and the amount of vacuum applied by the vacuum source is regulated as appropriate to control the width and thickness of the wet film of the coating material that is being applied to the substrate. By way of non-limiting example, controlling the width and thickness of the wet film can include maintaining the width and thickness at a certain value or within a range of values and/or changing the width and thickness. In one aspect, regulation of the vacuum source automatically occurs following a determination that the width of the wet film of coating material applied to the substrate falls outside of a predetermined range. Moreover, while described herein below in connection with the application of the coating material in the form of a reagent material to a web of substrate material from which a plurality of test elements will be obtained, it should be appreciated that the systems, apparatuses, techniques and processes disclosed herein may also be used in connection with the application of one or more different coating materials to one or more different types of substrates. Further aspects and features of the present application are described with respect to the illustrated embodiments as follows.

Referring to FIG. 1, there is illustrated a slot die coating apparatus 10 configured to apply a coating material 12 in the form of reagent material 14 (see FIG. 4 for example) to a web 16 of substrate material 18 from which a plurality of test elements are obtained. Apparatus 10 includes a plurality of rollers 20a-c through which web 16 is fed. More particularly, with reference to roller 20b for example, it is rotated in a clockwise direction as indicated by arrow A as web 16 is fed through apparatus 10. Apparatus 10 also includes a slot die assembly 22 positioned adjacent to roller 20b, a reservoir 21 fluidly coupled with slot die assembly 22 by conduit 21a and configured to hold a quantity of coating material 12, and a vacuum system 23 coupled with slot die assembly 22 by conduits 23a, only one of which is illustrated in FIG. 1. Further details of these features will be provided below in connection with FIGS. 2-5.

Figure 4:
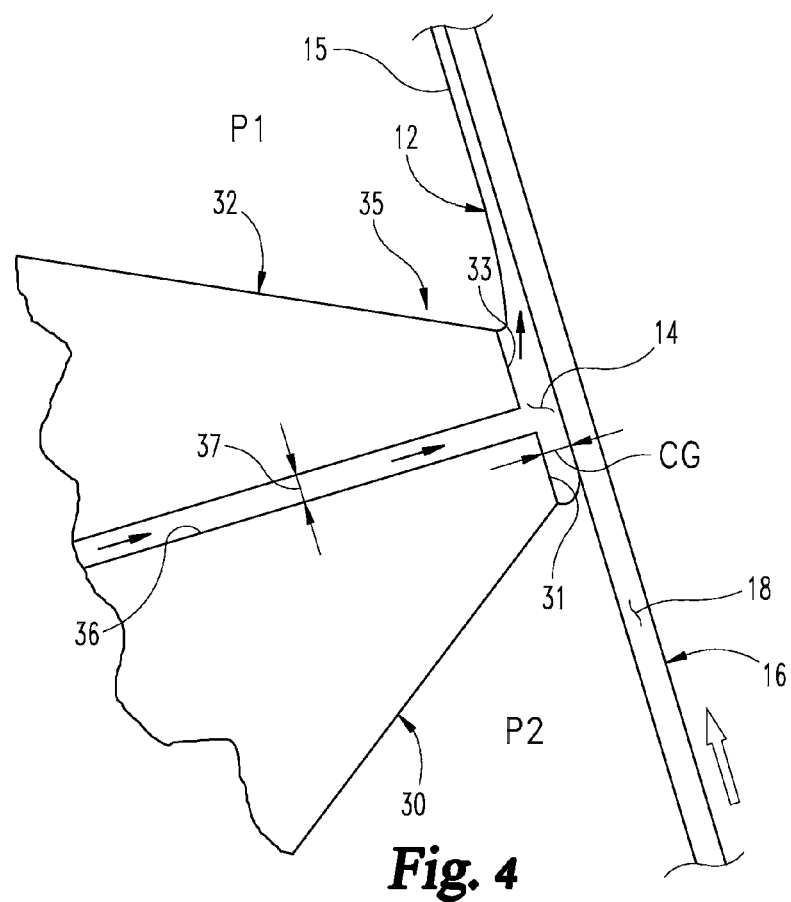
FIG. 4 is an enlarged, diagrammatic illustration of an operation for applying a coating material to a substrate with the slot die coating apparatus illustrated in FIG. 1.

More particularly, slot die assembly 22 includes a slot die head 26 and a housing 28 that cooperates with slot die head 26 and to which vacuum system 23 is coupled as will be discussed below. Slot die head 26 includes an upstream bar 30 positioned opposite of a downstream bar 32. As illustrated in FIG. 4 for example, slot die head 26 includes a discharge end 35 that includes a generally planar surface 31 on upstream bar 30 facing web 16 and a generally planar surface 33 on downstream bar 32 facing web 16. In the illustrated form, surface 31 is offset toward web 16 relative to surface 33, although forms in which surfaces 31, 33 are even or surface 33 is offset toward web 16 relative to surface 31 are also contemplated. A slot 36 is formed between upstream bar 30 and downstream bar 32 and opens through slot die head 26 adjacent to surfaces 31, 33. Slot 36 generally allows coating material 12 to be passed through slot die head 26 onto web 16, which is positioned between roller 20b and slot die head 26. In one form, upstream bar 30 and downstream bar 32 may be adjustably movable relative to one another to allow changes to the dimensions of slot 36 positioned therebetween. Further, in other non-illustrated forms, upstream bar 30 may include a drip bib 34 coupled therewith.

Figure 2:
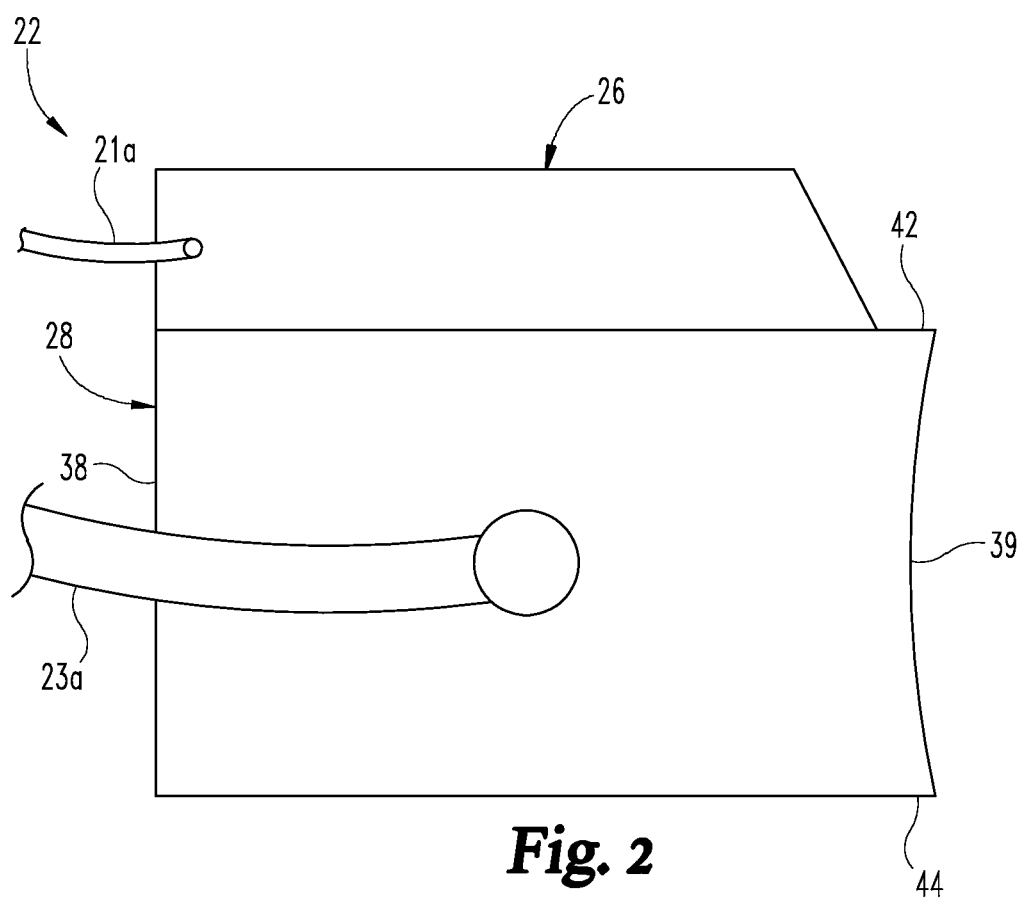
FIG. 2 is an enlarged, side plan view of a slot die assembly of the apparatus of FIG. 1.
Figure 3:
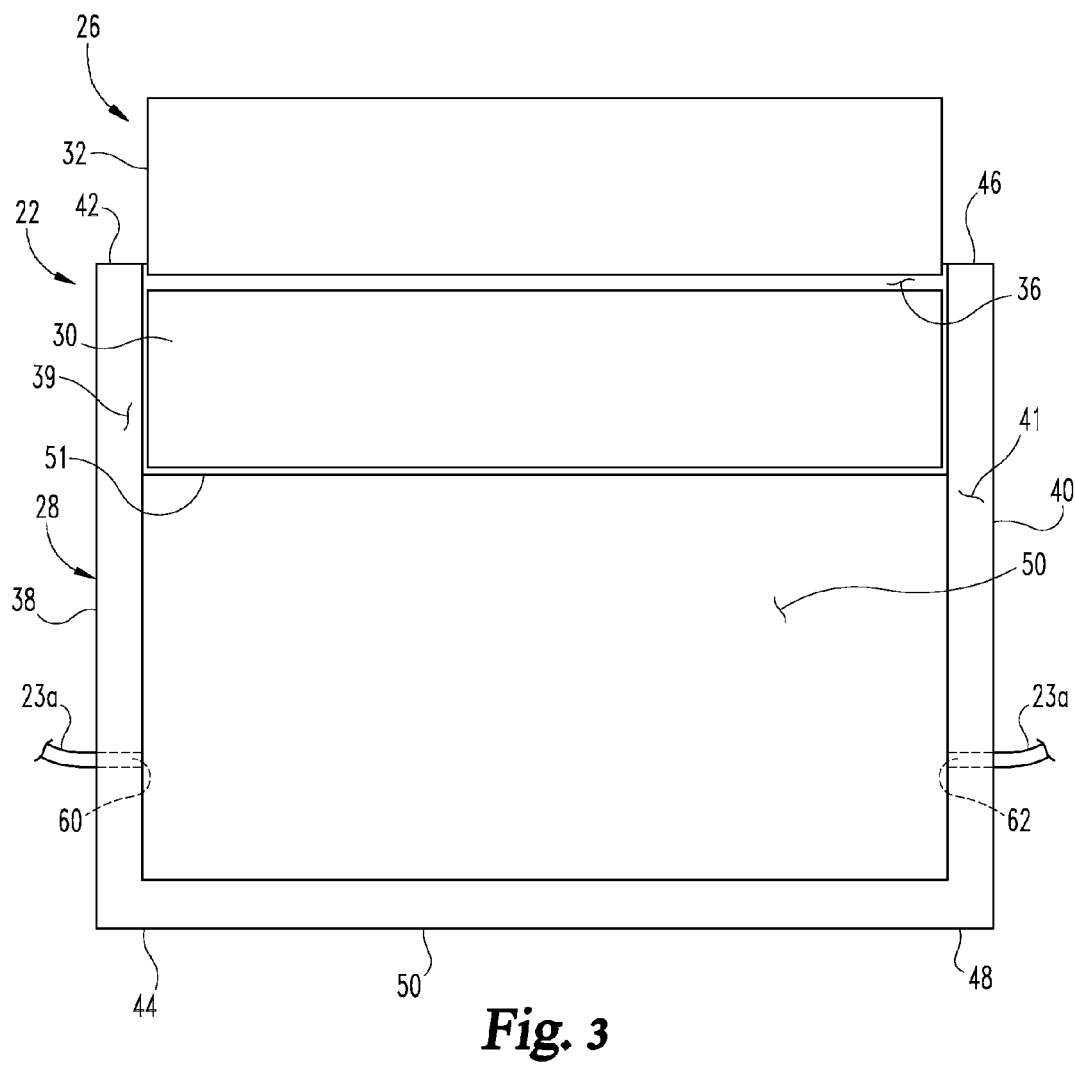
FIG. 3 is a front, plan view of the slot die assembly illustrated in FIG. 2 rotated ninety degrees relative to the view of FIG. 2.

Turning now to housing 28, it includes a pair of oppositely positioned lateral side panels 38, 40, with side panel 38 extending between a first end 42 and a second end 44 and side panel 40 extending between a first end 46 and a second end 48. As illustrated in FIG. 2 for example, side panel 38 includes a concavely shaped surface 39 extending between first end 42 and second end 44. In addition, side panel 40 also includes a surface 41 extending between first end 46 and second end 48 that is concavely shaped similar to surface 39. The concavity of surfaces 39, 41 is generally configured to correspond to the convexity of roller 20b such that side panels 38, 40 can be positioned against or in close proximity to roller 20b. However, in other non-illustrated forms, different configurations for surfaces 39, 41 are contemplated. As illustrated in FIG. 3 for example, upstream bar 30 and a portion of downstream bar 32 are positioned between side panels 38, 40 and between first ends 42, 46 and second ends 44, 48 thereof such that slot 36 is also positioned between side panels 38, 40 and between first ends 42, 46 and second ends 44, 48. A cross member 50 extends between side panels 38, 40 adjacent second ends 44, 48 on a first side of housing 28 facing roller 20b, and a back panel 51 extends between side panels 38, 40 on an opposite second side. In one or more non-illustrated forms, cross member 50 can include a recessed portion through which web 16 extends as it is moved along roller 20b. Cross member 50 may also include portions on opposite sides of the recessed portion, when present, which can be positioned against or in close proximity to roller 20b.

While not previously discussed, it should be appreciated that side panels 38, 40 and cross member 50 can be positioned in close proximity with roller 20b such that a generally enclosed environment or chamber 58 is provided upstream from slot 36. Further, as will be explained in greater detail below, surfaces 31, 33 of slot die head 26 are positioned in relatively close proximity to web 16. Similarly, this arrangement of slot die head 26 relative to web 16, as well as the discharge of coating material 12 from slot 36, generally encloses or seals chamber 58 adjacent to first ends 42, 46 of side panels 38, 40 as coating material 12 is applied to web 16. In view of the foregoing, it should be appreciated that chamber 58 is generally enclosed or sealed from the surrounding environment when coating material 12 is applied to web 16. It should be appreciated that it is not necessary for chamber 58 to be entirely sealed from the surrounding environment, although forms in which it is sealed in such a manner are also contemplated. Rather, it is generally sufficient for chamber 58 to be sealed or enclosed from the surrounding environment in a manner that allows air pressure within chamber 58 to be controlled relative to the surrounding environment, further details of which will be provided below. In one form for example, it is contemplated that housing 28 can be positioned relative to roller 20b such that a gap between about 5 μm and 250 μm extends between roller 20b and surfaces 39, 41. Forms in which housing 28 is positioned in contact with roller 20b are also contemplated. For example, in one form, surfaces 39, 41 of side panels 38, 40 and portions 54, 56 of cross member 50 can be formed of polytetrafluoroethylene (PTFE) or another suitable material that allows side panels 38, 40 and cross member 50 to be positioned against roller 20b while it is rotated. In another form, one or more rubber, silicone or other suitable seals can be positioned on surfaces 39, 41 and cross member 50 such that side panels 38, 40 and cross member 50 are positioned in close proximity or adjacent to roller 20b with the seals filling any gap therebetween.

Housing 28 also includes a pair of oppositely positioned outlets 60, 62 which open into chamber 58 opposite of one another and upstream from slot die head 26. In the illustrated form, outlets 60, 62 are coupled by conduits 23a with vacuum system 23 that is operable to regulate air pressure in chamber 58. More particularly, with reference to FIG. 5 for example, there is provided a diagrammatic illustration of one non-limiting form for vacuum system 23 that can be utilized for regulating air pressure in chamber 58. Vacuum system 23 includes a blower 72 that is coupled in fluid communication with baffle tank 74 by conduit 76. Blower 72 is generally configured to pull air toward it and away from baffle tank 74 to create a vacuum. In other non-illustrated forms, it is contemplated that the vacuum can be created using a pump or other sources in addition to or in lieu of blower 72. Conduits 23a extend from baffle tank 74 and are coupled with outlets 60, 62 of housing 28. Similarly, the vacuum applied to baffle tank 74 by blower 72 is transferable from baffle tank 74 through conduits 23a to chamber 58. System 23 also includes a conduit 82 that is coupled with and extends between a drain outlet of housing 28 and drain tank 84 and is operable to drain any liquid that may collect in housing 28.

System 23 further includes a flow control valve 86 that is positioned between blower 72 and baffle tank 74 and in communication with the vacuum force present in conduit 76 when blower 72 is operating. A breather 88 is positioned adjacent to control valve 86 and is operable to allow ambient air into conduit 76 in response to certain operations of control valve 86. For example, in one form, vacuum system 23 may include one or more sensors configured to determine the strength or level of the vacuum force in conduit 76, baffle tank 74 or chamber 58, just to provide a few non-limiting possibilities, and control valve 86 may be responsive to the one or more sensors to adjust the amount of ambient air allowed into conduit 76 to adjust the level of the vacuum force of system 23. In this or other forms, system 23 may also include one or more controllers, such as a frequency inverter driver, configured to control the operation of blower 72 such that the amount or force of the vacuum created by blower 72 is adjusted in response to the vacuum levels measured by the one or more sensors. As indicated above, the illustrated form of vacuum system 23 is non-limiting, and it should be further appreciated that other forms and arrangements are possible and contemplated for system 23.

Referring again to FIG. 4, further details regarding the application of coating material 12 to web 16 to form wet film 15 thereon will now be provided. It should be appreciated that housing 28 and roller 20b are not illustrated in FIG. 4 in order to enhance clarity. In addition, the following parameters and description are applicable to the application of coating material 12 in the form of reagent material 14 to web. Similarly, it should be appreciated that alternative values for the process parameters discussed below may be applicable to the slot die coating technique described herein for use with other forms of coating material 12 or upon the occurrence of other changes. In addition, it should also be appreciated that the below-described parameters may also change as the desired thickness T and width W (FIG. 6) of wet film 15 changes from the values described below.

Discharge end 35 of slot die head 26 is positioned in close proximity to web 16 such that a coating gap CG extends therebetween. In one non-limiting form, coating gap CG is between about 20 μm and about 600 μm. In another more particular form, coating gap CG is between about 40 μm and about 450 μm. Still, in another more particular form, coating gap CG is between about 40 μm and about 200 μm. However, it should be appreciated that alternative values for coating gap CG are possible and contemplated and can be affected by the rheology and weight of coating material 12, surface tension and speed of web 16, the radius of roller 20i, the lengths of upstream and downstream bars 30, 32 of slot die head 26, inlet gap and length of slot die head 26, and the angle, if any, of upstream bar 30 relative to the downstream bar 32.

In one form for applying reagent material 14, slot 36 includes a width between side panels 38, 40 between about 4 millimeters and about 10 millimeters. In another more particular form for applying reagent material 14, the width of slot 36 between side panels 38, 40 of housing 28 is 5 millimeters. In another more particular form for applying reagent material 14, the width of slot 36 between side panels 38, 40 of housing 28 is 7 millimeters. Still, other values for the width of slot 36 between side panels 38, 40 of housing 28 are possible. In addition, slot 36 also includes a height 37 between upstream bar 30 and downstream bar 32 between about 100 μm and about 300 μm. In particular forms where the width of slot 36 is 5 millimeters of 7 millimeters, height 37 is about 250 μm. As illustrated in FIG. 4 for example, slot die head 26 generally extends orthogonally to web 16 at the location where discharge end 35 is positioned adjacent thereto. However, in other forms it is also contemplated that slot die head 26 can extend obliquely relative to web 16. In addition, as best seen in FIG. 1 for example, slot die head 26 is oriented at an oblique angle relative to central axis 25 of roller 20b which, in one form, can be between about 10 degrees and about 25 degrees, although other variations are also contemplated.

As indicated above, web 16 is moved relative to slot die assembly 22 by rollers 20a-c of apparatus 10. In one form, web 16 is moved relative to slot die assembly 22 at a rate between about 35.0 m/min and about 45.0 m/min. In another more particular form, web 16 is moved relative to slot die assembly 22 at a rate between about 38.0 m/min and about 44 m/min, although other variations for the rate at which web 16 is moved are contemplated depending on the desired width and thickness of the coating relative to the particular application of the method and apparatus disclosed herein, and also depending on the flow rate of the discharged coating material. For example, in certain experimental coating processes described in greater detail below in the "EXAMPLES" section of the subject document, the web was moved relative to the slot die assembly at a rate between about 8.0 m/min and 12.0 m/min, and more particularly at a rate of about 10.0 m/min.

Figure 6:
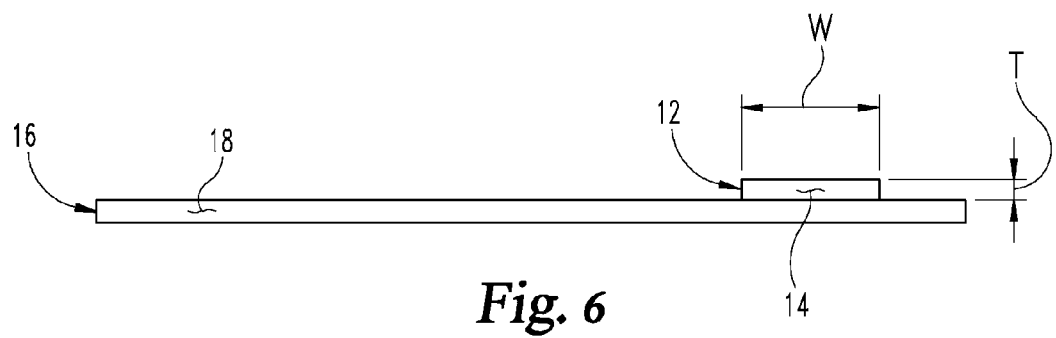
FIG. 6 is a side plan view of a substrate material on which a wet film has been formed.
Figure 5:
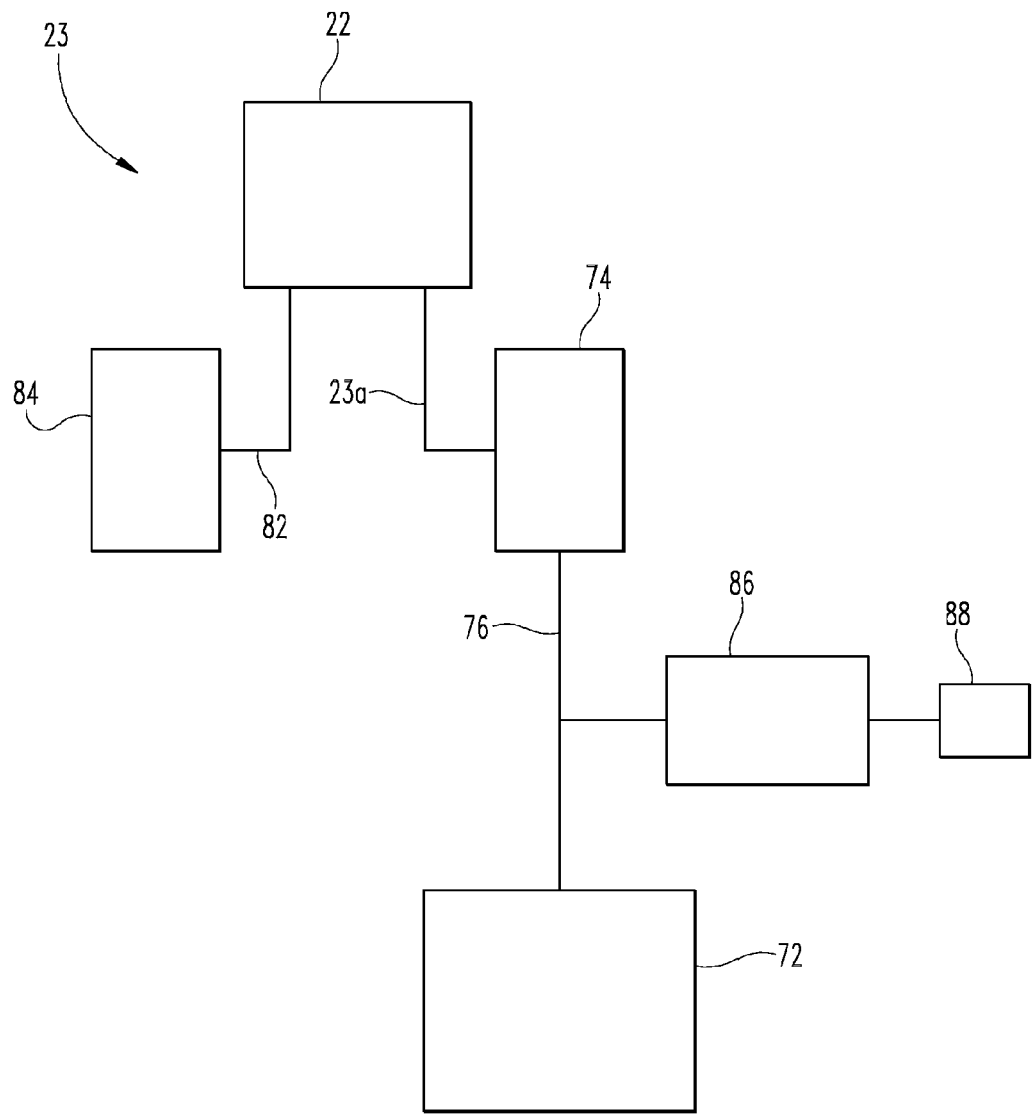
FIG. 5 is a diagrammatic illustration of a vacuum supply system configured to be coupled with the slot die assembly of FIG. 2.

As web 16 is moved relative to slot die assembly 22, coating material 12 is delivered to slot die head 26 from reservoir 21 using, by way of non-limiting example, one or more pumps, pistons, syringes, or bladder systems. Coating material 12 is forced through slot die head 26 and exits slot 36 at discharge end 35 where it is applied onto web 16 of substrate 18 to form wet film 15 which includes a width W and a thickness T relative to web 16 as illustrated in FIG. 6 for example. In one form, the discharge rate of coating material 12 from discharge end 35 is between about 10.0 mL/min and about 20.0 mL/min. In another more particular form, the discharge rate of coating material 12 from discharge end 35 is between about 12.0 mL/min and about 18.0 mL/min. In another form, the discharge rate of coating material 12 from discharge end 35 is between about 15.0 mL/min and about 18.0 mL/min. Still, other variations for the rate at which coating material 12 is discharged from discharge end 35 are also contemplated, and can be dependent on, amongst other things, the desired width and thickness of the coating relative to the particular application of the method and apparatus disclosed herein, and also on the rate at which web 16 is moved relative to slot die head 22. For example, in certain experimental coating processes described in greater detail below in the "EXAMPLES" section of the subject document, the discharge rate of coating material from the slot die head was between about 2.0 mL/min and about 4.0 mL/min.

In one form, the targeted width W of wet film 15 is between about 4 millimeters and about 8 millimeters. In a more particular form, the targeted width W of wet film 15 is between about 5 millimeters and about 7 millimeters. In another more particular form, the targeted width W of wet film 15 is between about 4.7 millimeters and about 5.3 millimeters. In still another more particular form, the targeted width W of wet film 15 is between about 6.7 millimeters and about 7.5 millimeters. In addition, in one form the targeted thickness T of wet film 15 is between about 20 μm and about 200 μm. In another more particular form, the targeted thickness T of wet film is between about 40 μm and about 100 μm. However, it should be appreciated that alternative values for the targeted width W and thickness T of wet film 15 are also contemplated.

FIG. 4 also illustrates that a first pressure P1 is present downstream of slot die head 26 and that a second pressure P2 is present upstream from slot die head 26. More particularly, first pressure P1 is indicative of ambient air pressure in the atmosphere surrounding apparatus 10, while second pressure P2 is indicative of air pressure in chamber 58 of housing 28. When vacuum system 23 applies a vacuum force to chamber 58, second pressure P2 is less than first pressure P1 and the difference between first pressure P1 and second pressure P2 defines a coating vacuum. In one form, the coating vacuum is between about 1 inch of $H_2O$ and about 10 inches of $H_2O$. In another form, the coating vacuum is between about 2 inches of $H_2O$ and about 9 inches of $H_2O$. In still another form, the coating vacuum is between about 1 inch of $H_2O$ and about 6 inches of $H_2O$. In yet another form, the coating vacuum is between about 1 inch of $H_2O$ and about 4 inches of $H_2O$. However, it should be appreciated that other values for the coating vacuum are contemplated and fall within the scope of the subject document.

It has been surprisingly discovered that adjustments to the coating vacuum can be used to control in real time the width W and thickness T of wet film 15 that will be applied to web 16. More particularly, increases in the amount of vacuum force applied to chamber 58 by vacuum system 23 will generally result in increases to the width W of wet film 15 that is formed by coating material 12 applied to web 16 following the increase in the amount of vacuum force. Moreover, it should be appreciated that, by way of non-limiting example, a 0.3 millimeter change to a 5.0 millimeter width W of wet film 15 will result in a 6% change in the thickness T of wet film 15. Similarly, regulating the width W of wet film 15 by controlling the amount of vacuum force applied to chamber 58 is an effective way of controlling the thickness T of wet film 15 along web 16. Further, the ability to control thickness T of wet film 15 in this manner provides an improved approach for achieving and maintaining relative consistency and uniformity in the thickness T of wet film 15 along web 16. Similarly, each of the test elements obtained from web 16 will have a more uniform thickness T of reagent material 14, thereby resulting in greater lot to lot consistency in the finished test elements.

Figure 7:
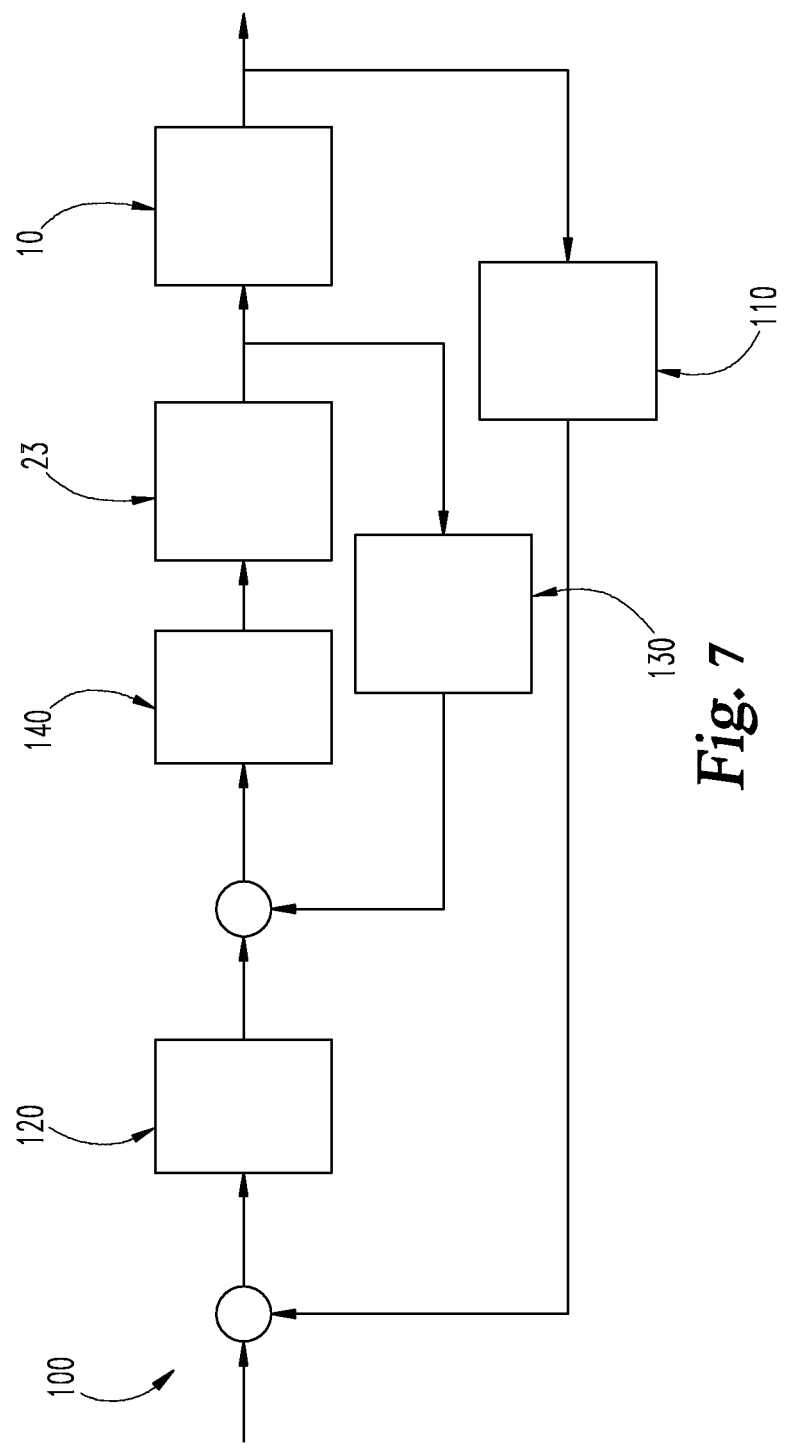
FIG. 7 is a diagrammatic illustration of a system for controlling operation of the slot die coating apparatus of FIG. 1 and vacuum supply system of FIG. 6.

One non-limiting approach for maintaining consistency and uniformity in width W, and in turn thickness T, of wet film 15 will now be described in connection with the schematic illustration of system 100 in FIG. 7. More particularly, system 100 includes apparatus 10, including vacuum system 23, each of which has been described above. System 100 also includes a sensor 110 for determining the width W of wet film 15 after it has been applied to web 16 by apparatus 10. In one form, sensor 110 can be an optical sensor, such as a digital camera, although other forms for sensor 110 are contemplated. Sensor 110 is also operable to generate a sensor signal corresponding to the determined width W of wet film 15 and transmit the sensor signal to a first controller 120. First controller 120 is programmed to determine if the width W of wet film 15 determined by sensor 110 corresponds to a value other than a predetermined value or range of values and, if so, transmit a corresponding controller signal to a second controller 140 indicating the changes that must be made to width W of wet film 15 in order to achieve a targeted thickness T of wet film 15 based on the following equation:

$$\text{Thickness } T = \frac{(\text{Coating Material Flow Rate})}{(\text{Web Speed})(\text{Width } W)}$$

In one form, the predetermined value for width W is 5 millimeters. In another form, the predetermined value for width W is 7 millimeters. In yet another form, the predetermined range of values for width W is from 2.5 to about 7.5 millimeters. In another form, the predetermined range of values for width W is from about 4.7 millimeters to about 5.3 millimeters. Still, in another form the predetermined range of values for width W is from about 6.7 millimeters to about 7.5 millimeters. However, it should be appreciated that other variations in the predetermined value or range of values for width W are possible.

Second controller 140 is generally programmed to control the amount of vacuum applied by vacuum system 23 in response to receiving from first controller 120 a controller signal indicating that changes must be made to width W of wet film 15 and/or in response to receiving a sensor signal from vacuum sensor 130 that is indicative that the actual amount of vacuum being applied to chamber 58 of housing 28 does not correspond to the amount of vacuum that should be applied thereto as determined by controller 140. In view of the foregoing, it should be appreciated that system 100 can, by way of non-limiting example, automatically and in real-time control the width W, and in turn thickness T, of wet film 15 that is applied to web 16. More particularly, in the event any width W of wet film 15 determined by sensor 110 does not correspond to the predetermined value or range of values, then the amount of vacuum applied by vacuum system 23 will automatically be adjusted as appropriate to bring width W of wet film 15 back to the predetermined value or within the range of predetermined values. Amongst other things, automatically adjusting the width W of wet film 15 in this manner results in a more uniform and consistent thickness T of wet film 15 along web 16, which in the case of reagent material 14, results in greater consistency between the individual test elements that will be obtained from web 14 to which wet film 15 is applied.

Figure 8:
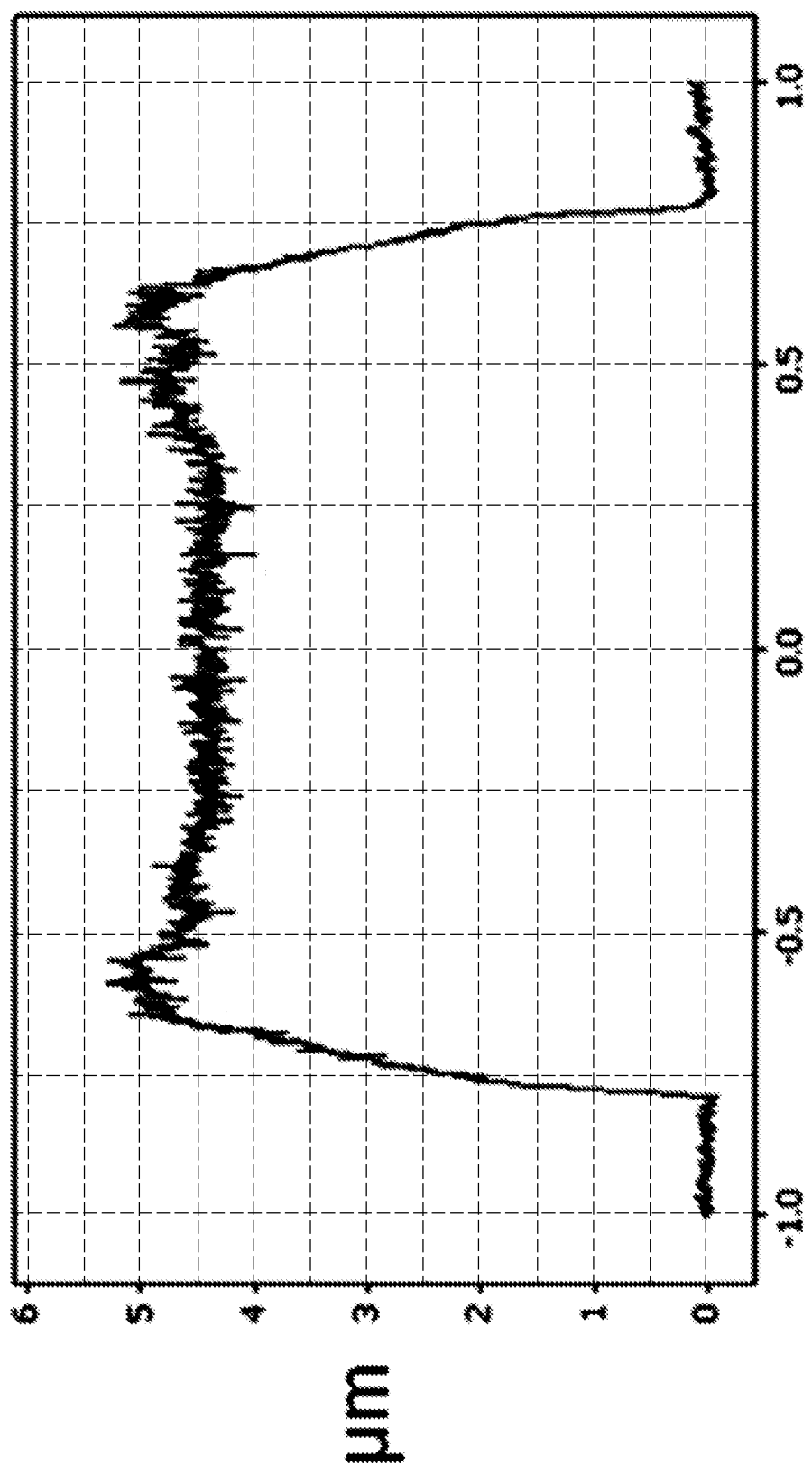
FIGS. 8-9 are graphical illustrations of the thickness profile of a layer of reagent material across its width.
Figure 9:
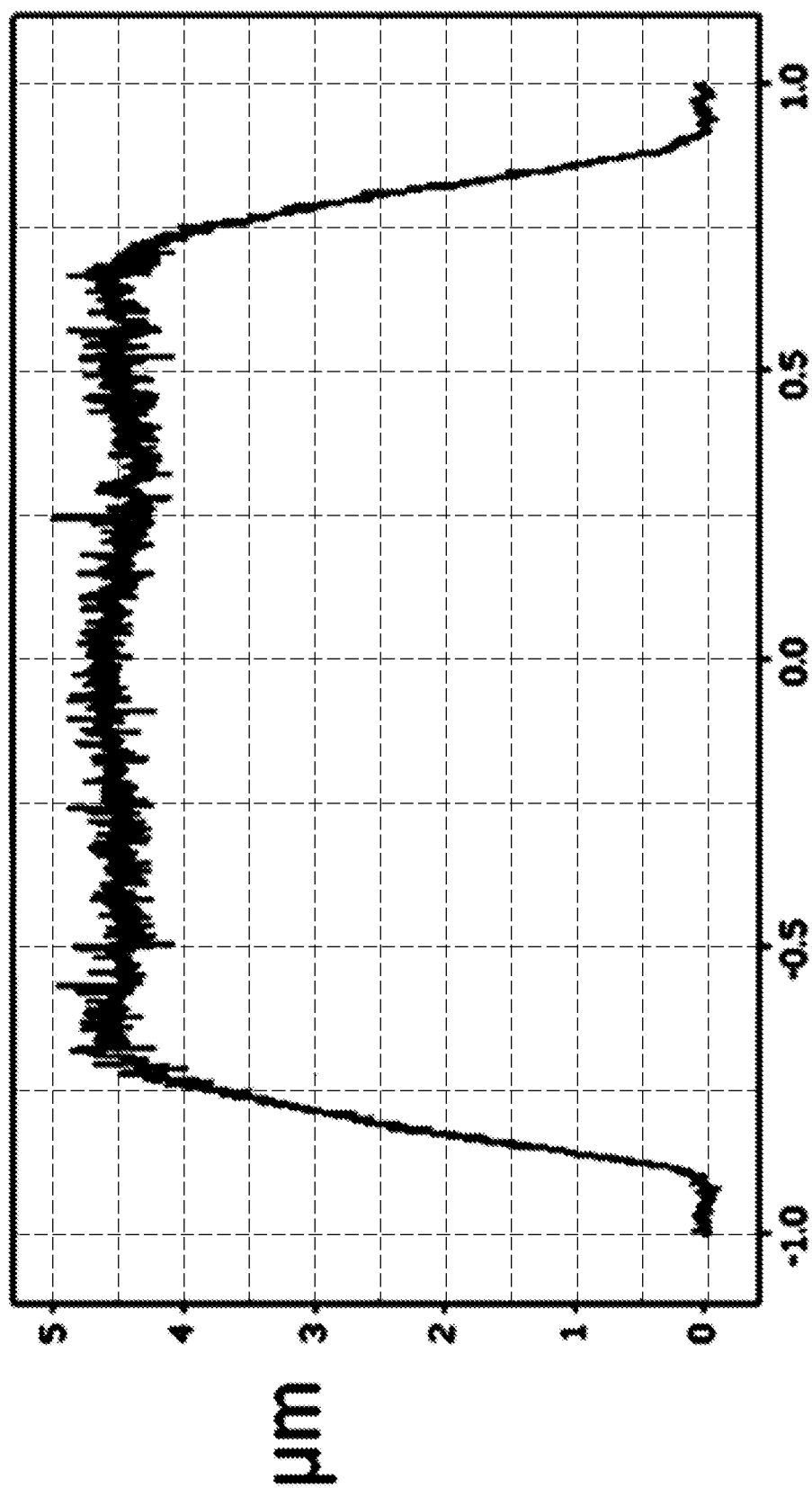

In addition to the foregoing, it has also been surprisingly discovered that controlling the amount of vacuum applied to chamber 58 to adjust thickness T of wet film 15 results in a more uniform thickness profile of reagent material 14 across the width of a reagent layer formed after wet film 15 dries. More particularly, FIG. 8 provides a graphical illustration of the thickness profile of reagent material 14 across the width of a dried stripe of reagent material 14 which has been formed on web 16 utilizing a coating gap CG in the range of 103-114 μm and without the application of any vacuum force to adjust width W and thickness T of the wet film. In contrast, FIG. 9 provides a graphical illustration of the thickness profile of reagent material 14 across the width of a dried stripe of reagent material 14 which has been formed on web 16 utilizing a constant 190 μm coating gap CG and the application of a vacuum force to control width W and thickness T of the wet film. As can be seen by comparing the graphical illustrations of FIGS. 8 and 9, the application of a vacuum force to control width W and thickness T of the wet film results in a more uniform and constant thickness T of reagent material 14 across the width of the dried stripe of reagent material 14.

In addition, while not previously discussed, it should also be appreciated that adjusting width W and thickness T of wet film 15 by controlling the amount of vacuum applied to chamber 58 also eliminates any need to move slot die head 26 relative to web 16 such that a constant coating gap CG can be maintained between said slot die head 26 and web 16 as coating material 12 is applied thereto. Furthermore, a constant flow rate of coating material 12 through slot die head 26 and a constant speed of web 16 relative to slot die head 26 can also be maintained when width W and thickness T of wet film 15 are adjusted by controlling the amount of vacuum applied to chamber 58. Likewise, the approach described herein conveniently only requires a change to be made to a single process parameter in order to adjust the width W and thickness T of wet film 15.

While not previously discussed, it should be appreciated that apparatus 10 and/or system 100 can be provided with additional features useful for processing web 16 either before or after the formation of wet film 15. For example, in one form, apparatus 10 also includes a dryer or drying mechanism that facilitates drying of wet film 15 to form a layer of reagent material 14. In one aspect, the dried layer of reagent material 14 includes a thickness relative to substrate 18 between about 1 μm and about 20 μm, between about 3 μm and about 20 μm, or between about 2 μm and about 10 μm, although other values for the thickness of the dried layer of reagent material 14 are also contemplated. Apparatus 10 may also include one or more cleaners or other components for preparing and/or processing web 16 for application of coating material 12. One or more cutting devices can also be included with apparatus 10 to cut web 16 into a plurality of test elements following the formation and drying wet film 15. In one form, the test elements include a length between about 20 millimeters and about 50 millimeters and a width between about 5 millimeters and about 15 millimeters. In a more particular form, the test elements include a length between about 33 millimeters and about 38 millimeters and a width between about 7 millimeters and about 9 millimeters.

As indicated above, the foregoing description regarding the application of coating material 12 has been made in connection with the formation of a wet film layer of reagent material 14 on web 16 of substrate material 18 from which a plurality of test elements will be obtained. Once formed, the test elements can be used in a system that is useful for assessing an analyte in a sample fluid. In one form, the analyte assessment may range from detecting the presence of the analyte to determining the concentration of the analyte. The analyte and the sample fluid may be any for which the test system is appropriate. By way of non-limiting example, one embodiment is described below in which the analyte is glucose and the sample fluid is blood or interstitial fluid. However, the assessment of other analytes in different sample fluids is also contemplated.

The test elements provide an electrochemical sensor including a sample-receiving chamber for the sample fluid, and reagent material 14 is suitable for producing an electrochemical signal in the presence of the test analyte. In one form, the test elements are in the form of disposable test strips. The test elements are used in combination with a meter for determination of the analyte in the sample fluid. The meter conventionally includes a connection with electrodes on the test elements and circuitry to evaluate the electrochemical signal corresponding to the concentration of the analyte. The meter may also include means for determining that the sample fluid has been received by the test element, and that the amount of sample fluid is sufficient for testing. The meter typically will store and display the results of the analysis, or may alternatively provide the data to a separate device. It will be appreciated by those of skill in the art that optical sensors (i.e. sensors configured with reagent material to produce an optical signal in the presence of an analyte) may also be produced according to the teachings herein, analogously to electrochemical sensors.

It is contemplated that the test elements may be useful for the determination of a wide variety of analytes. For example, the test elements may be readily adapted for use with reagent material 14 having any suitable chemistry that can be used to assess the presence of the analyte. In one specific form, the test elements are configured and used for the testing of an analyte in a biological fluid. Such analytes may include, for example, glucose, cholesterol, HDL cholesterol, triglycerides, lactates, lactate dehydrogenase, alcohol, uric acid, and 3-hydroxybutric acid (ketone bodies). Non-limiting examples of biological fluids in which the analyte can be assessed include any bodily fluid in which the analyte can be measured, such as interstitial fluid, dermal fluid, sweat, tears, urine, amniotic fluid, spinal fluid and blood. The term "blood" in the context of this document includes whole blood and its cell-free components, namely plasma and serum. When the test elements are configured for the testing of glucose, the sample fluid may specifically include, for example, fresh capillary blood obtained from the finger tip or approved alternate sites (e.g., forearm, palm, ear lobe, upper arm, calf and thigh), and fresh venous blood. In addition, the test elements may also be useful in connection with control fluids that are used in conventional fashion to verify the integrity of the system for testing.

The bodily fluid containing the analyte to be assessed may be acquired and delivered to the test elements in any fashion. For example, a blood sample may be obtained in conventional fashion by incising the skin, such as with a lancet, and then contacting the test element with fluid that appears at the skin surface. In one aspect, the test elements are operable for assessing the targeted analyte with only using very small fluid samples. Similarly, in one aspect, only a slight skin incision is necessary to produce the volume of fluid required for the test, and the pain and other concerns with such method can be minimized or eliminated.

The test elements which are formed from web 16 on which the layer of reagent material 14 is deposited include several basic components. More particularly, the test elements comprise a small body defining a chamber in which the sample fluid is received for testing. This "sample-receiving chamber" may be filled with the sample fluid by suitable means, such as by capillary action, but also optionally assisted by pressure or vacuum. The sample-receiving chamber includes electrodes and chemistry suitable for producing an electrochemical signal indicative of the analyte in the sample fluid.

Figure 10:
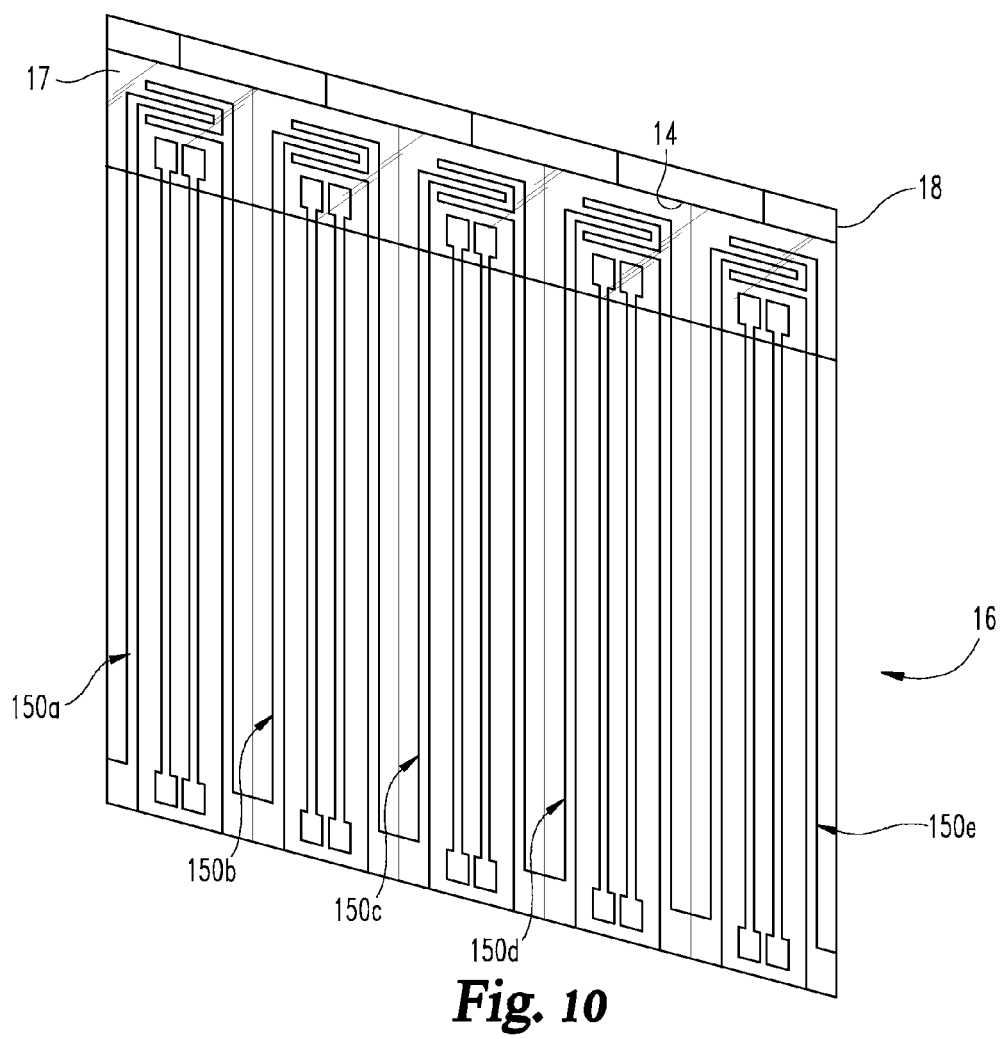
FIG. 10 is a perspective view of a portion of a web of substrate material from which a plurality of test elements will be obtained.

Referring now to FIG. 10 for example, a portion of web 16 is illustrated and includes a plurality of electrode systems 150*a-e* which will individually be included on separate test elements formed from the illustrated portion of web 16. Each of the electrode systems 150*a-e* includes a plurality of electrodes and electrode traces which terminate in contact pads. A portion of layer 17 of reagent material 14 overlies a portion of each of the electrode systems 150*a-e*. Similarly, it should be appreciated that reagent material 14 is applied to web 16 following the formation of electrode systems 150*a-e* thereon. Further details regarding the electrode systems 150*a-e*, as well as other aspects of the test elements and systems in which they are used, are provided in U.S. Pat. No. 7,727,467, the contents of which are incorporated herein by reference in their entirety. As also illustrated in FIG. 10, reagent layer 17 extends as a narrow stripe along the length of the illustrated portion of web 16 and across each of the electrode systems 150*a-e* positioned thereon.

Substrate material 18 of web 16 is formed of an insulating material on which electrode systems 150*a-e* are positioned. Typically, plastics such as vinyl polymers, polyimides, polyesters, and styrenes provide the electrical and structural properties which are required. Further, because the test elements can be mass producible from rolls of material, it is desirable that the material properties be appropriate to have sufficient flexibility for roll processing, while also giving a useful stiffness to the finished element. Substrate material 18 can be selected as a flexible polymeric material such as polyester, including high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). One specific possibility for substrate material 18 is MELINEX® 329 available from duPont.

The test elements are configured to detect the presence of, and/or measure the concentration of, an analyte by way of electrochemical oxidation and reduction reactions. These reactions are transduced to an electrical signal that can be correlated to an amount or concentration of the analyte. Similar, the electrode system on each test element includes a set of measuring electrodes, e.g., at least a working electrode and a counter electrode, that are positioned within the sample-receiving chamber. The sample-receiving chamber is configured such that sample fluid entering the chamber is placed in electrolytic contact with both the working electrode and the counter electrode. This allows electrical current to flow between the measuring electrodes to effect the electrooxidation or electroreduction of the analyte.

A "working electrode" is an electrode at which the analyte is electrooxidized or electroreduced with or without the agency of a redox mediator, while the term "counter electrode" refers herein to an electrode that is paired with the working electrode and through which passes an electrochemical current equal in magnitude and opposite in sign to the current passed through the working electrode. The term "counter electrode" is meant to include counter electrodes which also function as reference electrodes (i.e., counter/reference electrodes).

The working and counter electrodes, and the remaining portions of the electrode system, may be formed from a variety of materials. In one aspect, the electrodes should have a relatively low electrical resistance and should be electrochemically inert over the operating range of the test elements. Suitable conductors for the working electrode include gold, palladium, platinum, carbon, titanium, ruthenium dioxide, and indium tin oxide, and iridium, as well as others. The counter electrode may be made of the same or different materials, e.g., silver/silver chloride. In one specific embodiment, the working and counter electrodes are both gold electrodes.

The electrodes may be applied to substrate material 18 in any fashion that yields electrodes of adequate conductivity and integrity. Exemplary processes include sputtering and printing, just to provide a few non-limiting possibilities. In one specific form, gold electrodes are provided by coating substrate material 18 and then removing selected portions of the coating to yield the electrode system. One particular method for removing portions of the coating include laser ablation, and more particularly broad field laser ablation, as disclosed in U.S. Pat. No. 7,073,246, the contents of which are incorporated herein by reference in their entirety.

Laser ablative techniques typically include ablating a single metallic layer or a multi-layer composition that includes an insulating material and a conductive material, e.g., a metallic-laminate of a metal layer coated on or laminated to an insulating material. The metallic layer may contain pure metals, alloys, or other materials, which are metallic conductors. Examples of metals or metallic-like conductors include: aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or solid solutions of these materials. In one aspect, the materials are selected to be essentially unreactive to biological systems, non-limiting examples of which include gold, platinum, palladium, iridium, silver, or alloys of these metals or iridium tin oxide. The metallic layer may be any desired thickness which, in one particular form, is about 500 nm.

The electrode system may have a variety of configurations suited to the operation of the test elements and corresponding meter. In one form, the working and counter electrodes are positioned and dimensioned to minimize the volume of sample fluid required to cover them. In addition, the electrodes may also be configured to maintain a current flux of sufficient magnitude as to be measurable using a relatively inexpensive hand-held meter.

By way of further example, one specific form includes a counter electrode which extends around both sides of the working electrode. The counter electrode therefore has two elements, one in front of the working electrode and the other behind the working electrode, as the sample fluid enters the sample-receiving chamber. More specifically, the counter electrode includes elements which extend across the sample-receiving chamber. Each of these elements is about 250 µm wide. The working electrode element has a width of about 250 µm, and is spaced from each of the two counter electrode elements by about 255 µm. It should be appreciated however that the foregoing is only one of a number of configurations for the measuring electrodes.

The electrode traces and contact pads may be provided in a variety of fashions consistent with their intended function relative to the test element. These components of the electrode system may be composed of the same material as the electrodes, and are applied to the base substrate in the same manner and simultaneously with the application of the electrodes. In one specific embodiment, the traces and contact pads are gold, and are formed by laser ablation, particularly as described in U.S. Pat. No. 7,073,246, which was incorporated by reference herein above. However, alternate materials and methods of application may be employed.

Reagent material 14 is operable to react with the test analyte to produce the electrochemical signal that represents the presence of the analyte in the sample fluid. The reagent layer 17 can include a variety of active components selected to determine the presence and/or concentration of various analytes. The test chemistry is therefore selected in respect to the analyte to be assessed. As is well known in the art, there are numerous chemistries available for use with each of various analytes. For example, in one particular form, the reagent layer 17 can include one or more enzymes, co-enzymes, and co-factors, which can be selected to determine the presence of glucose in blood. In a more specific form where the analyte is glucose, the active components of reagent material 14 will typically include an oxidoreductase, such as an enzyme for glucose; optionally a co-enzyme or co-factor; and a redox mediator. These components are typically dissolved or suspended in a matrix. The liquid test sample hydrates or dissolves the matrix, and the analyte diffuses through the matrix to react with one or more of the active components. Typically, the enzyme oxidizes the glucose in the test sample to gluconolactone and/or gluconic acid. The mediator, in turn, reacts with or oxidizes the reduced enzyme, and consequently the mediator is reduced in the process. The reduced mediator can be detected at one of the electrodes on the test strip. More specific details regarding a specific form of reagent material 14 for determining the presence of glucose in blood are found in U.S. Pat. No. 7,727,467, the contents of which were incorporated herein above by reference in their entirety.

In conventional fashion, reagent material 14 may include a variety of adjuvants to enhance various properties or characteristics thereof. See e.g., U.S. Pat. No. 7,749,437 referred to hereinabove. For example, reagent material 14 may include materials to facilitate the placement of reagent material 14 onto web 16 and to improve its adherence to web 16, or for increasing the rate of hydration of reagent material 14 by the sample fluid. Additionally, reagent material 14 can include components selected to enhance the physical properties of the resulting dried reagent layer, and the uptake of a liquid test sample for analysis. Examples of adjuvant materials to be used with reagent material 14 include thickeners, viscosity modulators, film formers, stabilizers, buffers, detergents, gelling agents, fillers, film openers, coloring agents, and agents endowing thixotropy.

Non-limiting examples of thickeners that may be included in reagent material 14 include (1) starches, gums (e.g., pectin, guar gum, locust bean (carob seed) gum, konjac gum, xanthan gum, alginates, and agar), casein, gelatin, and phycocolloids; (2) cellulose and semi-synthetic cellulose derivatives (carboxymethyl-cellulose, methyl cellulose, hydroxymethylcellulose, hydroxyethylcellulose, methylhydroxyethylcellulose); (3) polyvinyl alcohol and carboxy-vinylates; and (4) bentonite, silicates, and colloidal silica. More specific forms of thickeners include a combination of a xanthan gum sold under the trade name Keltrol F by CP Kelco US, Inc., and carboxylmethyl cellulose sold under the trade name AQUALON® CMC 7F PH by Hercules Inc., Aqualon Division.

Film forming and thixotropic agents that can be included in reagent material 14 include polymers and silica. One more specific thixotropic agent includes silica sold under the trade name Kieselsaure Sipemate FK 320 DS by Degussa AG, while a more specific film forming agent includes polyvinylpyrrolidone, sold under the trademark polyvinylpyrrolidone Kollidon 25, by BASF, and polyvinyl propionate dispersion.

Stabilizers for the enzyme in reagent material 14 can be selected from sacchhrides and mono- or di-fatty acid salts. More specific stabilizers include trehalose sold under the trade name D-(+)-Trehalose dihydrate by Sigma Chemical Co. and sodium succinate.

Non-limiting examples of detergents that can be included in reagent material 14 include water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. More specific forms of detergents include an ester amide, n-octanoyl-N-methylglucamide, sold under the trade name Mega-8 by Dojindo Molecular Technologies, Inc., and a fatty acid salt, N-methyl oleyl taurate sodium salt, sold under the trade name Geropon T77 by Rhodia HPCII (Home, Personal Care and Industrial Ingredients).

In one form, reagent material 14 is formulated as a viscous solution that includes thickeners and thixotropic agents to enhance the physical properties of reagent layer 17. The thickeners are selected to provide a thick, liquid matrix having the remaining components homogeneously dispersed therein. The thickening and thixotropic agents also inhibit the liquid or semi-paste material from running or spreading over the surface of web 16 after it has been deposited and before it dries. After reagent material 14 is deposited, it quickly dries to a readily hydratable matrix.

An example of a test element that is configured for use with electrochemical techniques and includes a layer of reagent material that can be applied in accordance with the techniques disclosed herein is the ACCU-CHEK® Aviva test strip, which is described more fully in U.S. Pat. No. 7,727,467, the disclosure of which was incorporated herein above by reference in its entirety. This exemplary test element is distributed in the United States by Roche Diagnostics Corporation of Indianapolis, Ind.

EXAMPLES

The following examples are for illustration purposes and are not to be construed as limiting the invention disclosed in this document to only the embodiments disclosed in these examples.

Example I

The following examples are being provided to illustrate the relationship between flow rate, coating gap and vacuum parameters associated with the application of reagent material 14 to web 16. Each of Examples A-G set forth below indicates the vacuum that must be applied to maintain a 7 millimeter wet film width as the coating gap is increased at a plurality of different flow rates of reagent material 14 and with the substrate being moved relative to the slot die head at a rate of about 10 m/min.

Example A

| Reagent flow rate (mL/min) | Coating Gap Mean (μm) | Vacuum (Inches/$H_2O$) |
|---|---|---|
| 2.5 | 53.3 | 0 |
|  | 77.7 | 2.50 |
|  | 89.0 | 4.25 |
|  | 101.2 | 5.50 |
|  | 116.3 | 5.75 |
|  | 128.7 | 5.75 |
|  | 141.1 | 6.00 |

Example B

| Reagent flow rate (mL/min) | Coating Gap Mean (μm) | Vacuum (Inches/$H_2O$) |
|---|---|---|
| 2.6 | 63.5 | 0 |
|  | 74.8 | 2.75 |
|  | 89.5 | 4.80 |
|  | 101.9 | 5.50 |
|  | 114.4 | 5.50 |
|  | 126.9 | 5.75 |
|  | 139.3 | 5.50 |
|  | 152.0 | 5.50 |
|  | 164.2 | 5.60 |

Example C

| Reagent flow rate (mL/min) | Coating Gap Mean (μm) | Vacuum (Inches/$H_2O$) |
|---|---|---|
| 2.8 | 72.1 | 0 |
|  | 83.7 | 2.50 |
|  | 95.9 | 4.00 |
|  | 108.1 | 5.00 |
|  | 117.7 | 5.00 |
|  | 129.9 | 5.00 |
|  | 142.5 | 5.00 |
|  | 154.7 | 5.00 |
|  | 167.8 | 5.00 |

Example D

| Reagent flow rate (mL/min) | Coating Gap Mean (μm) | Vacuum (Inches/$H_2O$) |
|---|---|---|
| 3.0 | 70.2 | 0 |
|  | 82.0 | 2.50 |
|  | 94.4 | 3.80 |
|  | 106.3 | 4.10 |
|  | 118.6 | 4.50 |
|  | 131.1 | 4.50 |
|  | 143.5 | 4.75 |
|  | 156.2 | 4.75 |
|  | 194.1 | 5.00 |

Example E

| Reagent flow rate (mL/min) | Coating Gap Mean (μm) | Vacuum (Inches/$H_2O$) |
|---|---|---|
| 3.1 | 75.9 | 0 |
|  | 87.6 | 2.50 |
|  | 99.7 | 3.75 |
|  | 111.8 | 4.40 |
|  | 124.2 | 4.40 |
|  | 136.8 | 4.40 |
|  | 149.6 | 4.50 |
|  | 161.9 | 4.50 |
|  | 177.7 | 4.50 |

Example F

| Reagent flow rate (mL/min) | Coating Gap Mean (μm) | Vacuum (Inches/$H_2O$) |
|---|---|---|
| 3.3 | 76.7 | 0 |
|  | 88.1 | 2.00 |
|  | 100.2 | 3.10 |
|  | 112.5 | 3.75 |
|  | 124.5 | 4.20 |
|  | 136.9 | 4.10 |
|  | 149.7 | 4.10 |
|  | 161.9 | 4.10 |

Example G

| Reagent flow rate (mL/min) | Coating Gap Mean (μm) | Vacuum (Inches/$H_2O$) |
|---|---|---|
| 3.5 | 85.2 | 0 |
|  | 97.2 | 1.75 |
|  | 109.0 | 2.75 |
|  | 121.5 | 3.60 |
|  | 133.9 | 3.90 |
|  | 149.1 | 4.00 |
|  | 161.7 | 4.10 |
|  | 174.4 | 4.10 |
|  | 187.1 | 4.10 |

Figure 11:
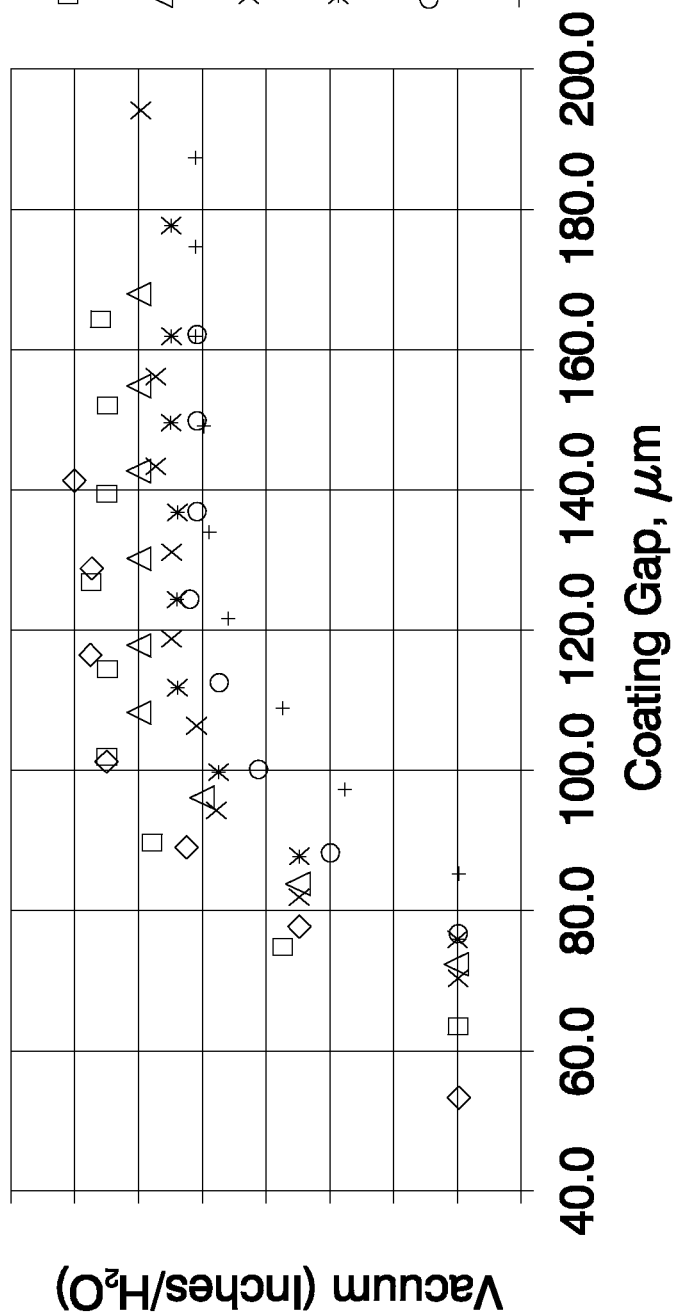
FIG. 11 is a graphical illustration representing the relationship between various process parameters of slot die coating techniques.

FIG. 11 further provides a graphical representation of the relationship between the parameters of each Examples A-G. As indicated above, these Examples are not to be construed as limiting the invention disclosed in this document. Moreover, it should also be appreciated that one or more of the values disclosed in these Examples may change as various process parameters, such as web speed and/or reagent flow rates, change.

In one embodiment, a technique for applying a coating material with a slot die apparatus includes adjusting air pressure around at least a portion of the discharge end of the slot die in order to control the width and thickness of a wet film of the coating material being applied to the substrate. Among other things, this technique allows the coating gap between the discharge end of the slot die and the substrate to be increased, which results in reduced wet film deformities, such as streaking, caused by debris trapped between the slot die and the substrate. Increased coating gaps also reduce the impact that variations in the substrate thickness have on the coating process. In addition, the ability to control the width and thickness of the wet film also increases thickness uniformity along the substrate and across the width of the wet film which, in the case of the substrate being used to form test elements for measuring the presence and/or concentrations of selected analytes in test samples, results in greater lot to lot consistency and accuracy in the test elements. Without being limited to any particular form, in one aspect of this embodiment the coating material comprises a reagent material for detecting the presence and/or concentration of glucose in a bodily fluid, such as blood. However, in other aspects it is also contemplated that the coating material could be any material suitable for application with a slot die coating process.

In another embodiment, a method for forming a narrow, continuous stripe or wet film of coating material having a width of less than about 9 millimeters and a thickness of less than about 100 µm on a substrate includes adjusting air pressure around at least a portion of a discharge end of a slot die in order to control the width and thickness of the wet film of the coating material on the substrate. One aspect of this embodiment includes maintaining constant one or more of the flow rate of the coating material, the coating gap between the slot die and the substrate, and the speed of the substrate relative to the slot die as the width and thickness of the wet film of the coating material are controlled. In another aspect of this embodiment, control of the width and thickness of the wet film includes one or both of maintaining a constant width and thickness of the wet film and changing the width and thickness of the wet film. In yet another aspect, the air pressure around at least a portion of the discharge end of the slot die is automatically adjusted in response to a determination that a portion of the wet film already applied to the substrate has a width that does not correspond to a predetermined value or fall within a range of predetermined values. In one form of this aspect, the air pressure is automatically adjusted in a manner that results in subsequently applied wet film having a width that corresponds to the predetermined value of falls within the range of predetermined values.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method for applying a wet film to a substrate, comprising:
    applying a coating material at a discharge rate about 2 ml/min to about 20 ml/min from a discharge end of a slot die onto a moving web of said substrate at a moving rate of about 10.0 m/min to about 45.0 m/min to form said wet film on said substrate, said wet film including a width and a thickness relative to said substrate, wherein said discharge end of said slot die comprises an upstream bar and a downstream bar each bar having an essentially planar land surface facing said moving web, and wherein a constant coating gap of about 40 µm to about 450 µm is maintained between said discharge end of said slot die and said moving web;
    applying a vacuum force adjacent said discharge end of said slot die, wherein said vacuum force creates a pressure differential between an upstream side of said discharge end and a downstream side of said discharge end, and wherein said pressure differential is between about 1 inch of $H_2O$ and about 10 inches of $H_2O$; and
    adjusting said vacuum force in real-time while applying said coating material to control said width and thickness of said wet film.

2. A method for applying a wet film to a substrate, comprising:
    applying a coating material at a discharge rate about 2 ml/min to about 20 ml/min from a discharge end of a slot die onto a moving web of said substrate at a moving rate of about 10.0 m/min to about 45.0 m/min to form said wet film on said substrate, said wet film including a width and a thickness relative to said substrate, wherein said discharge end of said slot die comprises an upstream bar and a downstream bar, each bar having an essentially planar land surface facing said moving web, and wherein a constant coating gap of about 40 µm to about 450 µm is maintained between said discharge end of said slot die and said moving web;
    applying a vacuum force adjacent said discharge end of said slot die, wherein said vacuum force creates a pressure differential between an upstream side of said discharge end and a downstream side of said discharge end, and wherein said pressure differential is between about 1 inch of $H_2O$ and about 10 inches of $H_2O$;
    adjusting said vacuum force in real-time while applying said coating material to control said width and thickness of said wet film; and
    sensing said width of said wet film, and wherein adjusting said vacuum force is performed in response to determining said width corresponds to a value other than a predetermined value.

3. The method of claim 2, wherein said predetermined value is about 5 millimeters.

4. The method of claim 2, wherein said predetermined value is about 7 millimeters.

5. The method of claim 2, wherein said predetermined value is between about 4.7 millimeters and about 5.3 millimeters.

6. The method of claim 2, wherein said predetermined value is between about 6.7 millimeters and about 7.5 millimeters.

7. The method of claim 1, wherein said substrate is formed of a polymer material on which a plurality of electrode patterns is positioned.

8. The method of claim 7, which includes applying said coating material from said discharge end of said slot die over said electrode patterns to form said wet film on said electrode patterns.

9. The method of claim 1, wherein applying said vacuum force includes positioning a vacuum box adjacent said discharge end of said slot die, said vacuum box including a pair of vacuum outlets positioned opposite one another and upstream from said wet film.

10. The method of claim 1, wherein said coating gap is between about 40 μm and about 200 μm.

11. The method of claim 1, wherein said coating material includes a reagent for producing an electrochemical signal in the presence of a test analyte.

12. The method of claim 11, wherein said test analyte is glucose and said reagent includes at least one of an enzyme, co-enzyme and co-factor.

13. The method of claim 1, wherein said thickness of said wet film is between about 40 μm and about 100 μm.

14. The method of claim 1, which further includes drying said wet film to provide a dried layer of said coating material on said substrate, said dried layer of said coating material including a dried thickness between about 3 μm and about 20 μm.

15. The method of claim 1, wherein said discharge rate is about 2 ml/min to about 4 ml/min.

16. The method of claim 1, wherein said moving rate is about 10 m/min.

17. The method of claim 1, wherein said coating gap is about 190 μm.

18. The method of claim 1, wherein said pressure differential is about 2 inches of $H_2O$ to about 6 inches of $H_2O$.

* * * * *